(12) United States Patent
Kumasaki et al.

(10) Patent No.: US 6,986,757 B1
(45) Date of Patent: Jan. 17, 2006

(54) SUCTION CONNECTOR AND SUCTION CATHETER USING THE CONNECTOR

(75) Inventors: Masahiko Kumasaki, Hiroshima (JP); Shusaku Azukizawa, Hiroshima (JP); Yoshihisa Ishihara, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 21 days.

(21) Appl. No.: 10/111,531

(22) PCT Filed: Oct. 30, 2000

(86) PCT No.: PCT/JP00/07654

§ 371 (c)(1),
(2), (4) Date: Apr. 23, 2002

(87) PCT Pub. No.: WO01/30416

PCT Pub. Date: May 3, 2001

(30) Foreign Application Priority Data

Oct. 29, 1999 (JP) .................................. 11/309258
Sep. 19, 2000 (JP) ............................. 2000-283661

(51) Int. Cl.
*A61M 1/00* (2006.01)
*A61M 5/00* (2006.01)
*A62B 9/04* (2006.01)

(52) U.S. Cl. ...................... 604/119; 604/248; 251/342; 128/202.27

(58) Field of Classification Search ............... 251/342, 251/354, 248, 902, 247, 31; 604/118–248, 604/43, 22; 427/355, 372; 399/340, 34; 128/202.27, 200.26; 137/505.13, 594
See application file for complete search history.

(56) References Cited

U.S. PATENT DOCUMENTS

| 3,933,177 | A | * | 1/1976 | Dwyer, Jr. .................. 137/861 |
| 4,534,542 | A | | 8/1985 | Russo |
| 4,589,869 | A | * | 5/1986 | Wernborg .................... 604/119 |
| 4,951,661 | A | * | 8/1990 | Sladek .................. 128/202.27 |
| 5,076,322 | A | * | 12/1991 | Choksi et al. ......... 137/505.13 |
| 6,712,095 | B2 | * | 3/2004 | Williamson et al. ........ 137/854 |

FOREIGN PATENT DOCUMENTS

| JP | 2-77049 U | 6/1990 |
| JP | 10-76001 A | 3/1998 |
| JP | 2567345 Y2 | 4/1998 |

* cited by examiner

*Primary Examiner*—Nicholas D. Lucchesi
*Assistant Examiner*—Roz Maiorino
(74) *Attorney, Agent, or Firm*—Hamre, Schumann, Mueller & Larson, P.C.

(57) ABSTRACT

A suction connector, comprising a fluid passage (31) having one end to be connected to a conduit and the other end to be connected to a suction source when in use and a ventilating passage (32) branched in the middle of the fluid passage and having an opening end (33), wherein a blocking plate (34) is disposed at least at a partial region on a fluid passage side inside the ventilating passage, the cross-section of the ventilating passage is divided by the blocking plate into a plurality of regions, and fluid advancing from the fluid passage into the ventilating passage is prevented by the blocking plate from flowing out from the opening end, whereby a sucking force caused by an releasing a negative pressure can be regulated sufficiently, spattering of fluid can be surely prevented to thus eliminate the danger of contamination and infection to an operator and assuring sanitation, and a structure is simplified.

6 Claims, 6 Drawing Sheets

FIG. 9A    Cross-section S2

FIG. 9B    Cross-section S1

SUCTION CONNECTOR AND SUCTION CATHETER USING THE CONNECTOR

TECHNICAL FIELD

The present invention relates to a suction connector used for a medical suction catheter for sucking a body fluid etc. In particular, it relates to a suction connector capable of controlling the start and stop of suction.

BACKGROUND ART

A major surgery commonly is carried out under general anesthesia. At this time, in order not to induce the respiratory arrest, maintenance of the airway is carried out by inserting a tracheal catheter into the oral cavity of a patient. In such a case, in order to suppress the production of saliva, a drug such as atropine sulfate generally is administered. In order to suck and remove the saliva or sputum that is nevertheless produced, a suction catheter often is used. Furthermore, in an open-heart surgery or an abdominal operation, the suction catheter is useful for sucking and draining (and in certain cases, reusing) a body fluid such as blood or effusion, etc. coming out from an affected site such as a wound site.

However, a conventional suction catheter had some disadvantages in use as follows.

First, when a body fluid is sucked and removed while bringing a suction catheter into contact with an affected site, the tip of the catheter sucks upon the living tissue due to a "sucking phenomenon" and cannot be detached therefrom frequently. In such a case, conventionally, by pinching the suction catheter by the finger to close it or by bending the suction catheter, the suction force is weakened to thus eliminate the sucking phenomenon. However, when the catheter has a small diameter or a large wall thickness, a bore thereof cannot be closed sufficiently by the finger, and so the suction phenomenon cannot be eliminated sufficiently in many cases. In such cases, by bending the catheter, the bore is closed. However, in this method, an operator has to use both hands, thus making the work inconvenient.

Therefore, a suction catheter provided with a side hole serving as a ventilating port at a base end of the catheter has been devised. In this suction catheter in use, during suction, an operator closes the side hole by the finger, and opens the side hole when the sucking phenomenon occurs. Thereby, the negative pressure is released, thus eliminating the sucking phenomenon. However, with this catheter, since sputum, blood, or the like, is attached to the finger used for closing the side hole during suction, it is not sanitary. Besides this, a suction catheter provided with connector having a complicated for weakening the suction force has been devised, but it is expensive and hard to be commercialized.

Furthermore, JP 5 (1993)-51351U discloses a suction connector in which a ventilation port is filled with a cylindrical filter made of a synthetic resin, which allows gases to pass through but does not allow liquid to pass through. This structure is intended to obtain a function of preventing liquid from scattering by the filter. However, with this suction connector, a sufficient amount of suction cannot be secured. Furthermore, in the case where the regulation of the suction speed and the suction amount is carried out frequently or over a long time, contaminant enters into the filter mesh along the longitudinal direction thereof, so as to prevent the ventilation of gas in the direction from the ventilating port to the fluid passage. Consequently, the reduction of the suction force by releasing a negative pressure may be insufficient.

As mentioned above, in the conventional configuration, it has not been possible to obtain a suction catheter having both functions of releasing a negative pressure and preventing liquid from scattering that are balanced to a practically sufficient extent; having a simple structure; and being cheap. Moreover, in order to obtain the sufficient function of releasing a negative pressure, it is necessary to broaden a cross-section of the ventilating passage and a suction regulating aperture, that is, an opening end of the ventilating passage. However, if the cross-section of the ventilating passage and a suction regulating aperture are broadened, the scattering amount is increased, thus making it difficult to provide a suction catheter with both functions.

DISCLOSURE OF THE INVENTION

It is an object of the present invention to provide a suction connector and a suction catheter using the same in which a sucking force can be regulated sufficiently by releasing a negative pressure, scattering of fluid can be prevented surely to thus eliminate the danger of contamination and infection on an operator and assuring sanitation, and a structure is simplified to be cheap.

A suction connector of the present invention includes a fluid passage having one end to be connected to a conduit and the other end to be connected to a suction source when in use and a ventilating passage branched in the middle of the fluid passage and having an opening end. In order to solve the above-mentioned problems, in the suction connector of the present invention, blocking plates are disposed at least at a partial region on a fluid passage side inside the ventilating passage, the cross-section of the ventilating passage is divided into a plurality of regions by the blocking plates, and fluid advancing from the fluid passage to the ventilating passage is prevented from flowing out from the opening end by the blocking plates. Moreover, in the present invention, the fluid includes not only liquid such as saliva, blood and effusion but also viscous fluid such as sputum.

According to the above-mentioned configuration, since the liquid entering the ventilating passage collides against the blocking plates to be returned to the fluid passage, the liquid does not flow out from the opening end of the ventilating passage beyond the blocling plates. Therefore, liquid is not attached to the finger pushing the opening end of the ventilating passage and there is no danger of contamination or infection on an operator. Furthermore, even if the blocking plates are provided, the function of releasing a negative pressure by the ventilating passage is lost only at a practically negligible level.

In the above-mentioned configuration, it is preferable that the blocking plates are disposed in the region excluding the proximity of the opening end.

Furthermore, it is preferable that a plurality of regions on the cross-section of the ventilating passage are divided so that the regions are arranged in the axial direction of the fluid passage.

Furthermore, it is preferable that the blocking plate is disposed with inclination toward the side to which the conduit is connected with respect to the direction of the fluid passage.

Furthermore, it is preferable that the axis direction of the ventilating passage is inclined toward the side to which the conduit is connected with respect to the axial direction of the fluid passage.

Furthermore, it is preferable that the blocking plate includes two plates or more and an end of the plate at the fluid passage side and an end of the plate at the opening portion side have an overlapped portion seen from the direction perpendicular to the fluid passage, or face in line to each other.

The suction catheter of the present invention uses a suction connector having any one of the above-mentioned suction connectors and has one end connected to a conduit.

BRIEF DESCRIPTION OF DRAWINGS

FIGS. 5A and 5B are enlarged cross-sectional view showing the structure of blocking plates, and FIGS. 5A and 5B show different examples of the blocking plates, respectively.

BEST MODE FOR CARRYING OUT THE INVENTION

First Embodiment

Hereinafter, a suction connector in the first embodiment of the present invention and a suction catheter to which the suction connector is attached will be explained with reference to FIGS. 1 to 5.

Figure 1:
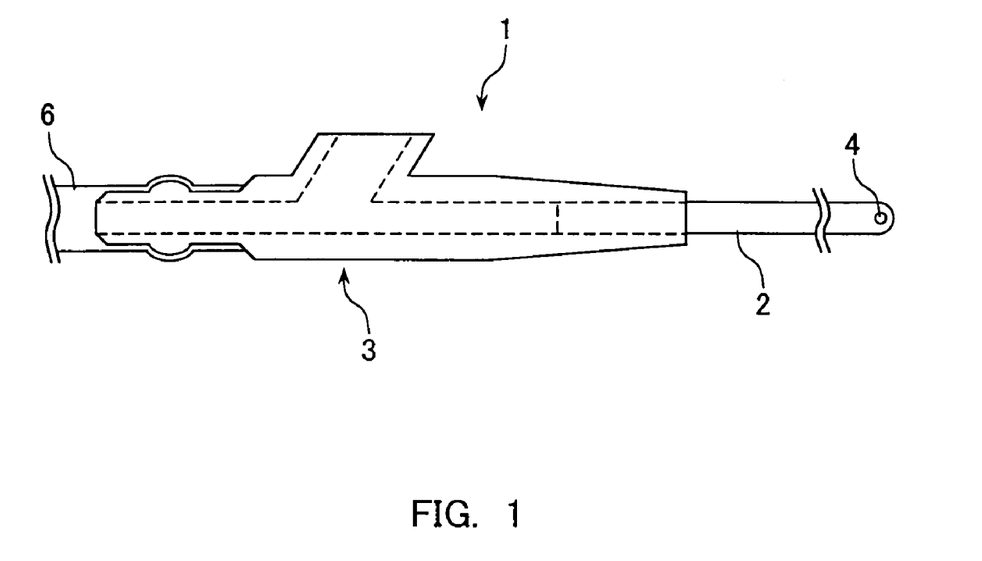
FIG. 1 is an elevational view showing a suction catheter in a first embodiment of the present invention.

As shown in FIG. 1, a suction catheter 1 includes a flexible conduit 2 and a suction connector 3 attached to the base end side of the conduit 2. At the tip of the flexible conduit 2, one or a plurality of suction holes 4 are provided and a body fluid etc. is sucked through the hole(s). At the other end of the suction connector 3, an extension tube 6, which is to be connected to a suction source in use, can be linked.

Figure 2:
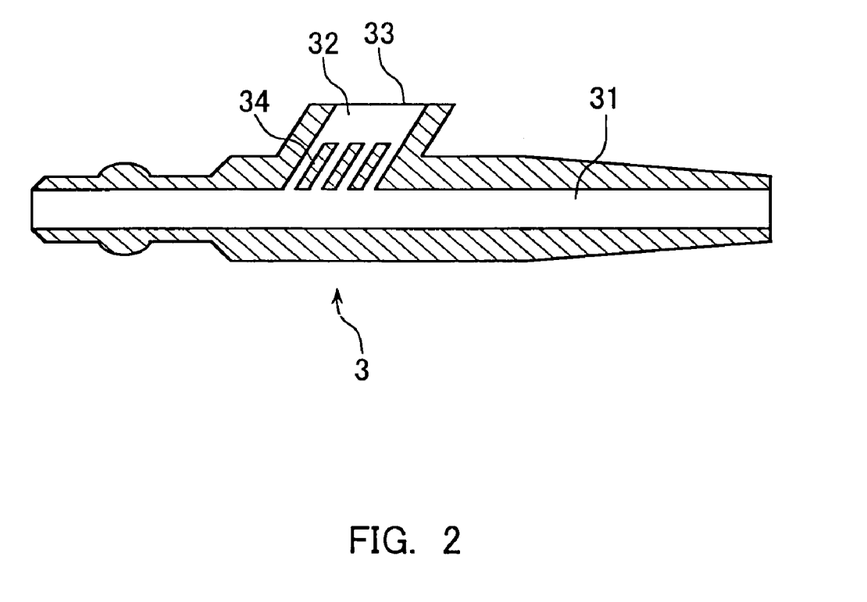
FIG. 2 is an elevational cross-sectional view showing a suction connector used in the suction catheter shown in FIG. 1.

As shown in FIG. 2, the suction connector 3 includes a fluid passage 31 and a ventilating passage 32 branched in the middle of the fluid passage 31 and having an opening end 33 (suction regulating port). The ventilating passage 32 provides a function of releasing a negative pressure in the fluid passage 31. During suction, an operator adjusts the opening/closing of the opening end 33 with a finger to change the degree of releasing a negative pressure, thus controlling the suction amount and suction speed of fluid. When the sucking phenomenon of the catheter occurs, the opening end 33 is opened so as to eliminate the sucking phenomenon. Inside the ventilating passage 32, blocking plates 34 are provided. The blocking plates 34 are provided for preventing the fluid advancing into the ventilating passage 32 from flowing out of the opening end 33 and has a function of preventing the liquid from scattering. Thereby, it is possible to prevent fluid from attaching to the finger of an operator.

In this embodiment, the blocking plates 34 include three plates. Both ends of each plate are supported by the inner wall of the ventilating passage 32 and cross over the ventilating passage 32. The blocking plates 34 are disposed at a partial region on a fluid passage 31 side inside the ventilating passage excluding the proximity of the opening end 33. Therefore, the ventilating passage 32 in this region is divided into a plurality of regions arranged in the axial directions of the fluid passage 31 by the blocking plates 34. Each plate has a sufficient resistance to a negative pressure generated inside the catheter during suction or a flowing pressure of outside air sucked by the suction source when the opening end 33 is opened.

Figure 3:
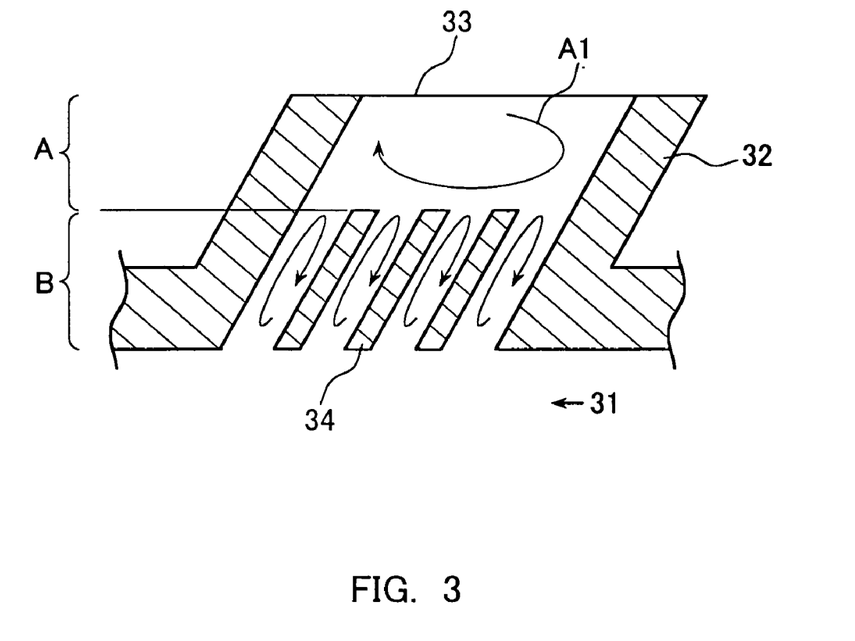
FIG. 3 is an enlarged cross-sectional view to illustrate the operation of a ventilating passage of the suction connector shown in FIG. 2.

The details of the effect of the blocking plates 34 on the fluid advancing into the ventilating passage 32 are not clear but thought to be as follows. First, a main factor of fluid advancing into the ventilating passage 32 includes turbulence of gas generated inside the ventilating passage 32 when the opening end 33 is opened/closed. By providing the blocking plates 34 inside the ventilating passage 32, as shown in FIG. 3, a space A that is distal relative to the fluid passage 31 and a space B that is proximal relative to the fluid passage 31 are provided inside the ventilating passage 32. Therefore, it is thought that large turbulence A1 generated in the space A does not reach the fluid passage 31 and acts to prevent the fluid from being drawn into the ventilating passage 32 or as reducing the degree thereof.

By providing the blocking plates 34 in this way, a great effect of preventing liquid from scattering can be obtained. By the way, a function of releasing a negative pressure depends on the area of the cross-section and the opening end of the ventilating passage 32. Basically, the effect of releasing a negative pressure is limited by a minimum cross-sectional area portion and is increased as the minimum cross sectional area is larger. On the other hand, as the minimum cross sectional area is larger, the danger of increasing the amount of scattering the fluid may be larger. When the blocking plates 34 are provided, the portion where the blocking plates 34 are disposed becomes the minimum cross-sectional area portion and in this portion, the level of the effect of releasing a negative pressure and the effect of preventing fluid from scattering are determined. It is noted that when the blocking plates 34 are provided, the rate at which the effect of preventing liquid from scattering is improved by the blocking plates 34 is larger than the rate at which the minimum area is reduced by the blocking plates 34. In other words, even if the minimum cross-sectional area is equal, when the blocking plate 34 is provided, the scattering amount is smaller as compared with the case where the blocking plates 34 are not provided. That is, with an equal function of releasing a negative pressure, a higher function of preventing liquid from scattering can be provided. Therefore, by providing the blocking plates 34, it is possible to balance well both the function of releasing a negative pressure and the function of preventing liquid from scattering.

The blocking plates 34 are not necessarily limited to the embodiment shown in FIG. 2 as long as it has the above-mentioned effects. For example, as is apparent from the above-mentioned explanation with reference to FIG. 3, the blocking plates 34 can have an appropriate function of preventing liquid from scattering even if they are not inclined. Furthermore, an appropriate effect can be obtained even if the length of the blocking plate 34 in the axial direction of the ventilating passage 32 is shorter. However, it is desirable that the effective area of the plate is sufficiently large in order to exhibit the function of preventing fluid from attaching to the finger by preventing even a very small amount of fluid that advances into the ventilating passage 32 from reaching the opening end 33 or by also preventing the fluid from reaching the opening end 33 due to other factors.

Figure 4:
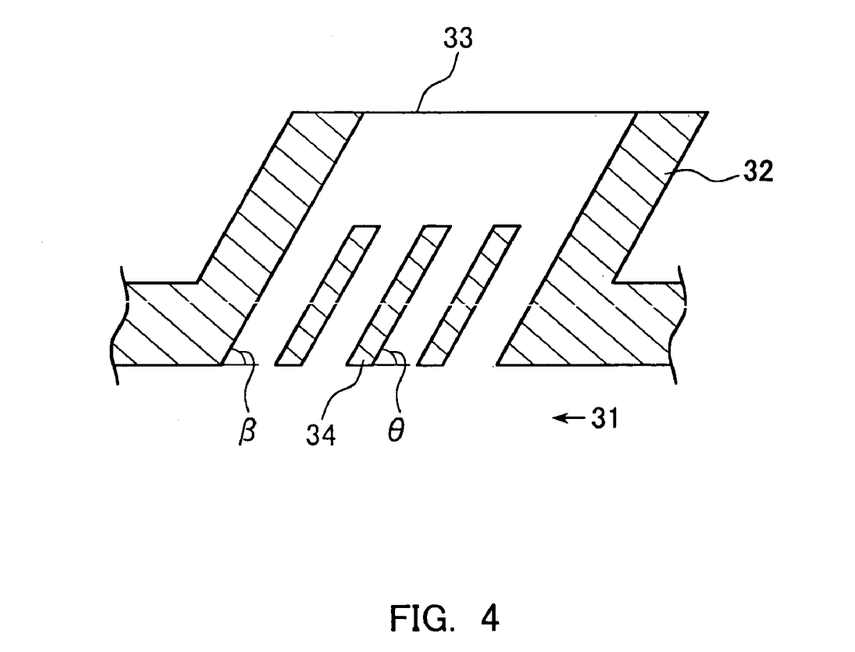
FIG. 4 is an enlarged cross-sectional view showing the structure of a ventilating passage of the suction connector shown in FIG. 2.

As a shape of the blocking plate 34, as shown in FIG. 2, etc., it is desirable that the plates are disposed with inclination in the direction of the fluid passage 31 in order to obtain a higher effect of preventing liquid from scattering. The inclining direction is made so that the plates are inclined toward the side where the flexible conduit 2 is connected, that is, the direction opposite to the suction source. As shown in FIG. 4, it is preferable that the plates 34 are disposed so that the inclining angle θ of the blocking plate 34 is not more than the inclining angle β of the inside wall of the ventilating passage 32, that is, θ<β should be satisfied. Since the fluid is likely to advance in the direction toward the suction source side of the ventilating passage 32, by disposing the plates as mentioned above, the more efficient effect of preventing liquid from scattering can be obtained. Practically, it is preferable that the inclining angle θ of the blocking plate 34 is equal to the inclining angle β of the inside wall of the ventilating passage 32 (θ=β). Thereby, it is possible not only to allow fluid to collide reliably with the plates but also to form the connector into one piece by one injection molding, thus providing a suction connector that can be manufactured easily and is cheap.

Figure 5A:
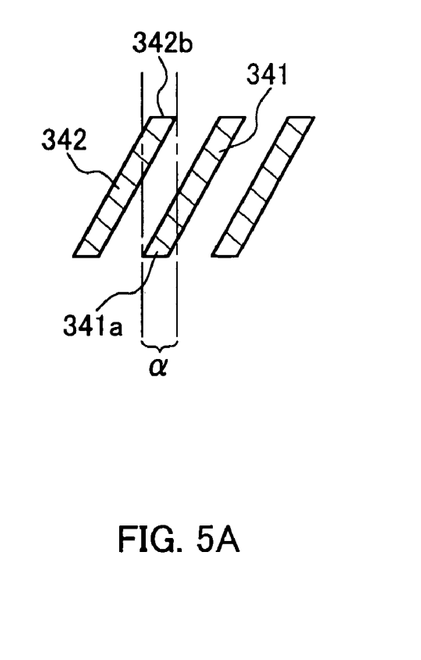
Figure 5B:
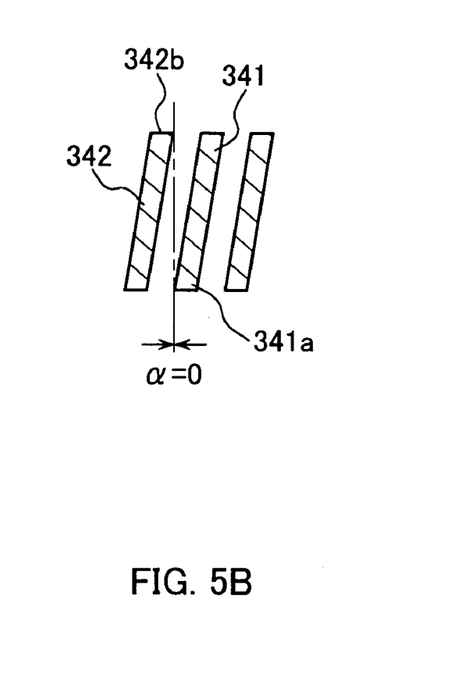

It is preferable that the plates constituting the blocking plates 34 are positioned relative to each other as shown in FIGS. 5A and 5B. In the example shown in FIG. 5A, seen from the direction perpendicular to the fluid passage 31, the end 341a at the fluid passage side of the plate 341 and the end 342b at the opening end side of the neighboring plate 342 have an overlapping portion α. The example shown in FIG. 5B shows the position relationship in which the end 341a at the fluid passage side of the plate 341 is brought into contact with the end 342b at the opening end side 342b of the neighboring plate 342 (α=0). With this arrangement, since there is no gap between the plates, there is an effect of preventing the fluid, which advances into the ventilating passage 32 toward the upper portion of the direction perpendicular to the fluid passage 31, from passing through.

Figure 6:
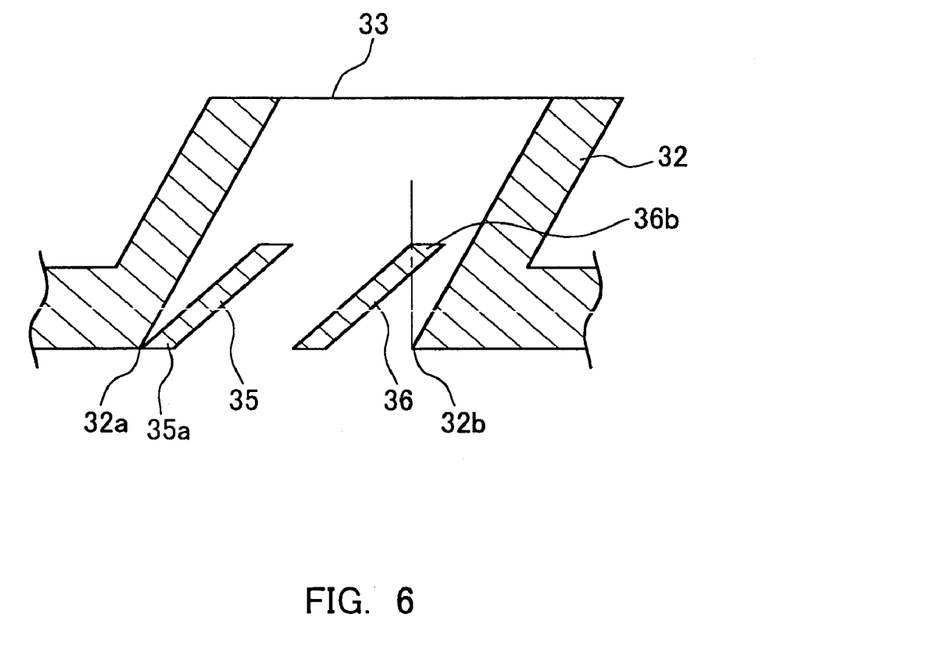
FIG. 6 is an elevational cross-sectional view showing another example of the blocking plates disposed in a ventilating passage of a suction connector.

Furthermore, it is preferable that the blocking plates 34 and the inside wall of the ventilating passage 32 are configured so that the positional relationship shown in FIG. 6 is satisfied. That is, the end 35a at the fluid passage side of the plate 35 is formed continuously with the end 32a at the fluid passage side of the inside wall at the suction source side of the ventilating passage 32. The end 36b at the opening portion side of the plate 36 is formed extending to the flexible conduit side seen from the direction perpendicular to the fluid passage 31 with respect to the end 32b at the fluid passage side of the inside wall of the flexible conduit side of the ventilating passage 32. Furthermore, the plate 35 and the plate 36 have an overlapped portion a as shown in FIG. 5 or face in line with each other (α=0). With such a configuration, the blocking plates direct liquid entering from any one of the suction source side, the flexible conduit side of the ventilating passage 32, or the central portion in the opening portion of the branched portion of the ventilating passage 32 to return to the fluid passage 31 side.

The number of the plates constituting the blocking plate 34 is not particularly limited, and the number may be one or two or more. The plate thickness necessary to provide the sufficient pressure resistance property is different depending upon the material. The number of the plates may be set in an appropriate range with the ventilating path necessary to regulate the excellent ventilation and the thickness of the plate taken into account.

Second Embodiment

Figure 7A:
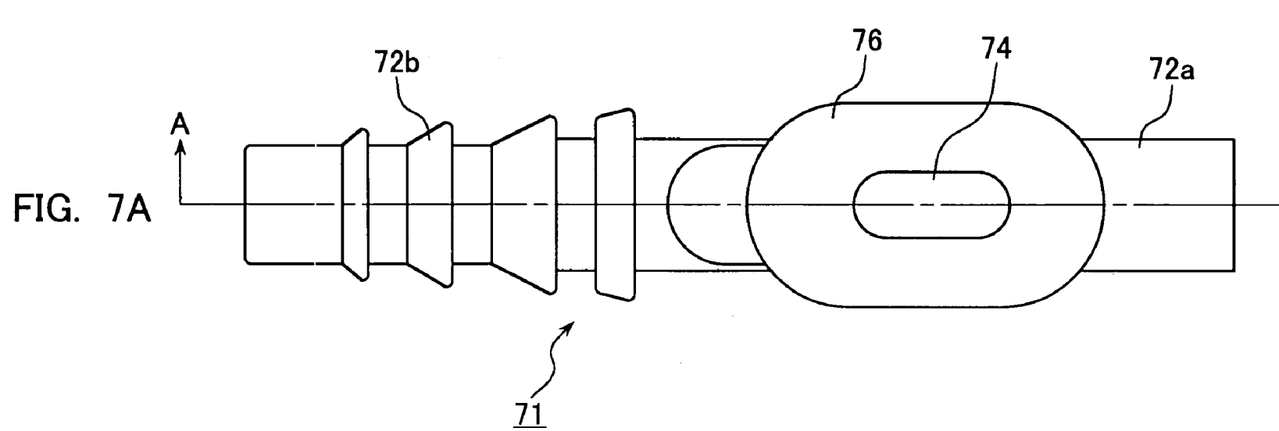
FIG. 7A is a plan view showing a suction connector in a second embodiment of the present invention.
Figure 7B:
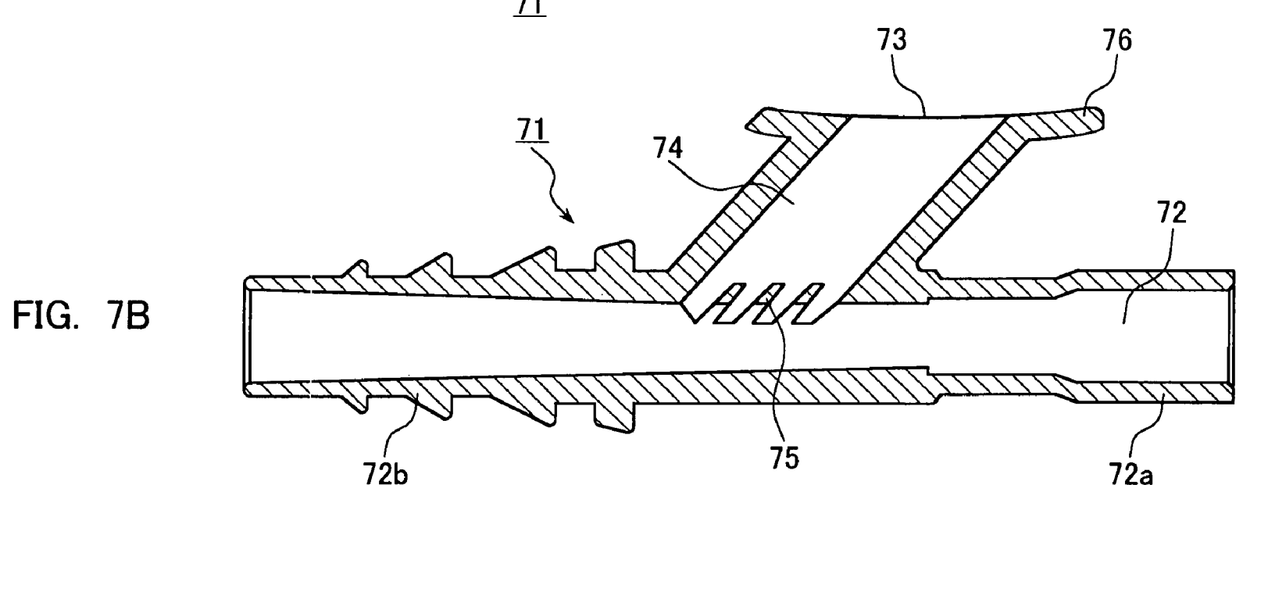
FIG. 7B is an elevational cross-sectional view thereof.

The suction connector in the second embodiment of the present invention will be explained with reference to FIGS. 7 and 8. FIG. 7A is a plan view showing a suction connector 71 in this embodiment; and FIG. 7B is a cross-sectional view of the FIG. 7A along the line A—A.

The suction connector 71 includes a fluid passage 72 and a ventilating passage 74 branched in the middle of the fluid passage 71 and having an opening end 73 (opening portion for regulating the suction). Blocking plates 75 are provided inside the ventilating passage 74. The fluid passage 72 has a flexible conduit connecting portion 72a to be connected to a flexible conduit (not shown in the drawing) and a suction source connection portion 72b capable of being linked to an extending tube (not shown in the drawing) to be connected to the suction source. The basic operation of the suction connector 71 is the same as the suction connector 3 in the First Embodiment.

Figure 8:
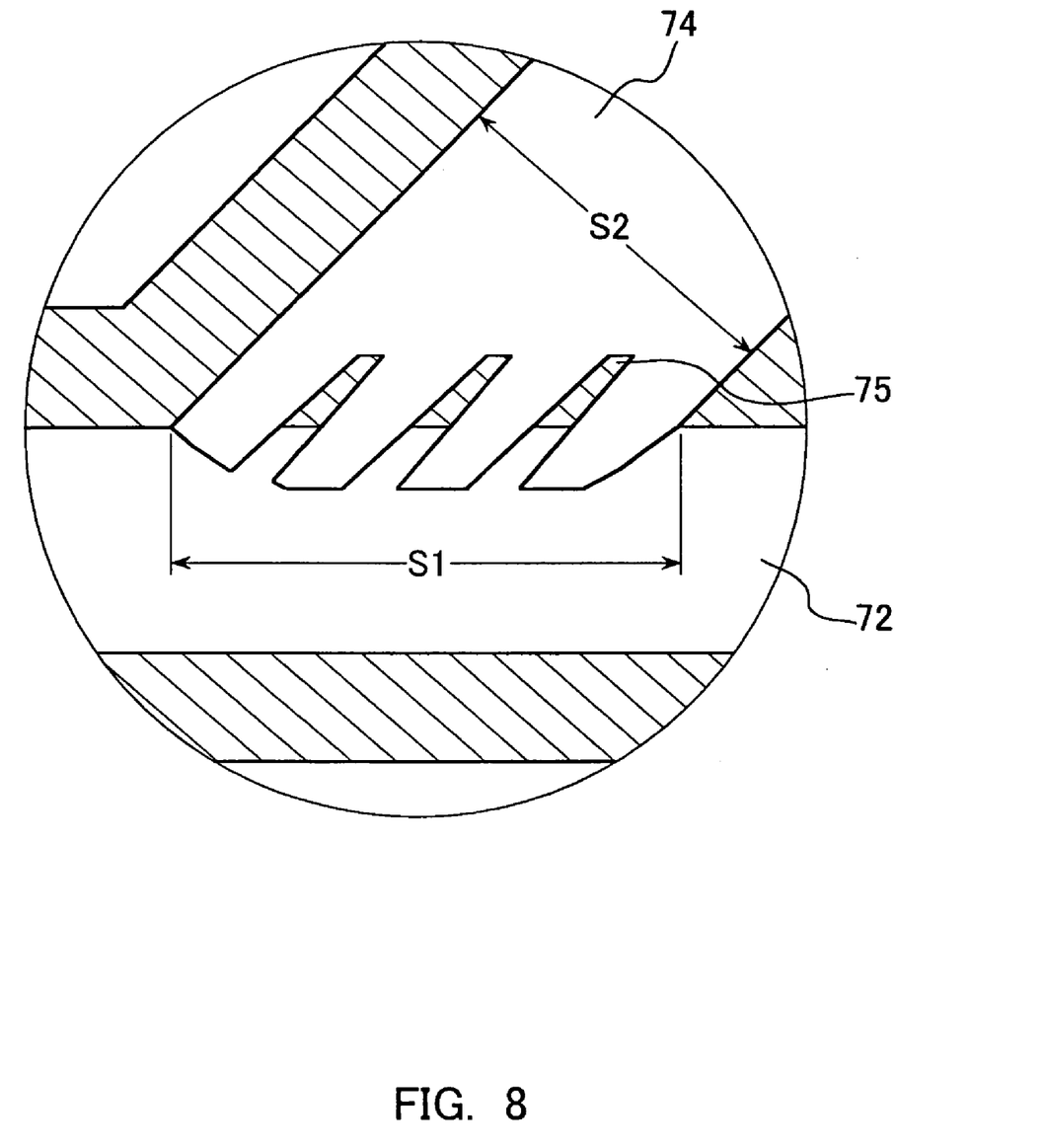
FIG. 8 is an enlarged cross-sectional view showing a part of the blocking plates of the suction connector shown in FIG. 7.
Figure 9A:
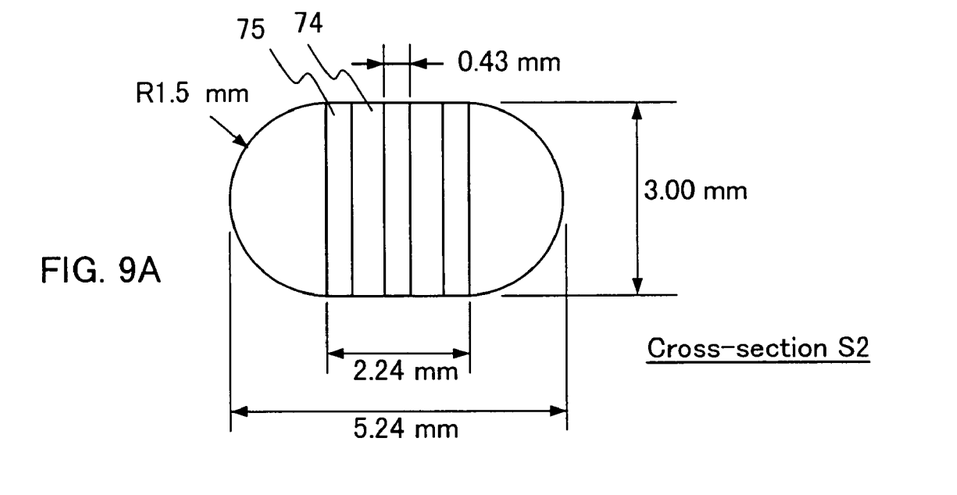
FIG. 9 is a cross-sectional view showing a shape of the cross sections S2 and S1 shown in FIG. 8.
Figure 9B:
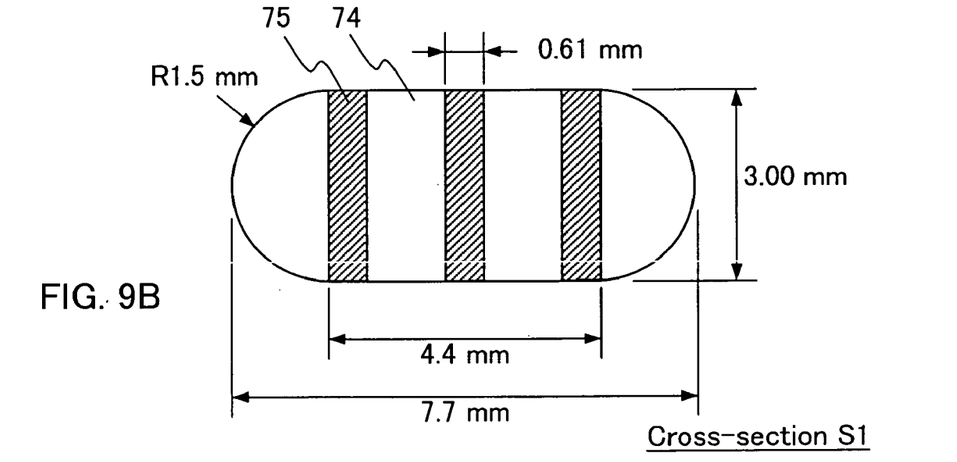

FIG. 8 is an enlarged cross-sectional view showing the blocking plate 75 and the peripheral portion thereof shown in FIG. 7. S1 in FIG. 8 shows a cross section inside the ventilating passage 74 in which the ventilating passage 74 is opened to the fluid passage 72. S2 shows a cross section inside the ventilating passage 74, which is perpendicular to the axis of the ventilating passage 74. The cross-sectional shape of the ventilating passage 74 is oval as shown in FIG. 9. FIG. 9A shows the shape of the ventilating passage 74 and the blocking plate 75 in the cross section S2; and FIG. 9B shows the shape of the ventilating passage 74 and the blocking plate 75 in the cross section S1.

The opening end 73 is provided with a flange 76. The stop 76 is provided so that an operator can touch and slide across the opening end 73 so as to regulate the open/close degree. Thereby, it is possible to carry out the fine regulation easily.

In the suction connector 71 of this embodiment, the size of the blocking plates 75 are relatively small as compared with those shown in FIG. 2 in the first embodiment. That is, the proportion of the region in which the blocking plates 75 are present in the ventilating passage 74 is rather small. Furthermore, as is apparent from the cross section shown in FIG. 8, the plates constituting the blocking plate 75 do not have an overlapped portion a as shown in FIG. 5. The neighboring plates are arranged separately from each other so that the end of the plate at the fluid passage side does not face in line to the end of the plate at the opening end side. Even with such an arrangement, it is possible to exhibit the sufficient function of preventing liquid from scattering. In a word, no problem occurs insofar as the function of releasing a negative pressure and the function of preventing liquid from scattering are balanced with respect to the suction pressure in the range in use. Thus, the blocking plates 75 can enhance the function of preventing liquid from scattering without adversely affecting the function of releasing a negative pressure.

The function of preventing liquid from scattering by the blocking plates 75 was confirmed by the following experiments for examining the effect of releasing a negative pressure and the effect of preventing liquid from scattering by the suction connector.

The shape of the suction connector was assumed to be the same as that shown in FIG. 7 and the narrowest diameter of the fluid passage 72 was set to be 3 mm. The dimension of the cross-section S1 and the cross section S2 were set to be those shown in FIG. 9. The angle of the ventilating passage 74 with respect to the fluid passage 72 was set to be 45 degrees. The thickness of the plates constituting the blocking plate 75 was in the range from 0.28 to 0.43 mm; and the length of the ventilating passage 74 in the direction of the axis thereof was set to be 1.5 mm. Furthermore, the same suction connector except that it dose not have the blocking plate 75 was prepared. Moreover, the minimum cross-sectional area of the ventilating passage 74, that is, the area obtained by subtracting the area of the blocking plates from the area of the cross-section S2 when the blocking plate are provided, was 9.9 $mm^2$, and the area of the cross section S2 when the blocking plates were not provided was 13.8 $mm^2$.

The evaluation of the effect of preventing liquid from scattering was carried out as follows. First, the suction operation was carried out by putting the tip of the catheter into/from the water 20 times so that water and air are mixed assuming that the catheter is used. In order to measure the scattering amount of the sucked water, a cellophane tape, to which a filter paper had been attached in advance, was prepared and attached to the opening end 73. The total weight of the cellophane tape to which the filter paper had been attached was measured before and after the suction operation. The difference between the measured weights before and after the suction operation was assumed to be the amount of scattering water. The suction pressure was set to be 26.7 kPa.

The function of releasing a negative pressure was evaluated as follows. The tip of the catheter was fixed in water and suction was carried out with the opening end 73 opened. At this time, the increased height of the liquid surface in the catheter was measured. The measurement value was assumed to be a residual negative pressure value and it was subjected to evaluation. The measurement was carried out at each suction pressure of 20.0, 28.0, 41.3, 61.3 and 93.3 kPa.

As a result of the above-mentioned experiments, the amount of scattered liquid of the suction connector without the blocking plates is 3–4 times that of the suction connector having blocking plates. The residual negative pressure values was higher by 0.01 to 0.03 kPa in the suction connector having blocking plates when the residual negative pressure values were 41.3, 61.3 and 93.3 kPa. However, when the suction pressure was 20.0 and 28.0 kPa, there is no difference between both connectors and the residual negative pressure value was 0 Pa. Since the generally used suction pressure is 20.0 to 26.7 kPa for adults and 16.0 to 20.0 kPa for children, the above-mentioned results show that the function of releasing a negative pressure of the suction connector having a blocking plate is practically sufficient.

Moreover, when the thickness of the blocking plate is the same, it is assumed that the effect of releasing a negative pressure is not changed. Therefore, by adjusting the height of the blocking plate (the length of the ventilating passage in the direction of the axis) in accordance with the usage modes, the function of preventing liquid from scattering can be regulated.

INDUSTRIAL APPLICABILITY

According to a catheter of the present invention to which a suction connector is attached, since liquid advancing into a ventilating passage collides with a blocking plate and is caused to return to the fluid passage, liquid can be prevented from flowing out of an opening end of the ventilating passage beyond the blocking plate. Therefore, since the liquid is not attached to the operator's finger pushing on the opening end of the ventilating passage, there is no danger of contamination or infection to the operator, enabling a treatment safely and sanitarily. In addition, the function of releasing a negative pressure can be secured sufficiently. Furthermore, the suction connector according to the present invention has a simple structure and thus can be provided cheaply.

The invention claimed is:

1. A suction connector, comprising
a fluid passage having one end to be connected to a conduit and the other end to be connected to a suction source when in use;
and a ventilating passage branched in the middle of the fluid passage and having an opening end,
wherein a blocking plate is disposed inside the ventilating passage in a region adjacent to the fluid passage, except for a region adjacent to the opening end, and
the blocking plate extends in an axial direction of the ventilating passage so that the cross-section in traverse direction of the ventilating passage is divided by the blocking plate into a plurality of regions arranged in an axial direction of the fluid passage, whereby fluid flowing through the fluid passage is prevented by the blocking plate from flowing to the opening end.

2. The suction connector according to claim 1, wherein the blocking plates are disposed in the region excluding the proximity of the opening end.

3. The suction connector according to claim 1, wherein the blocking plate is inclined toward the side to which the conduit is connected with respect to the direction of the fluid passage.

4. The suction connector according to claim 1, wherein the axial direction of the ventilating passage is inclined toward the side to which the conduit is connected with respect to the axial direction of the fluid passage.

5. The suction connector according to claim 3, wherein the blocking plate comprises two plates or more and an end of the plate at the fluid passage side and an end of the plate at the opening portion side have an overlapped portion with each other seen from the direction perpendicular to the fluid passage or are brought into contact with each other.

6. A suction catheter using a suction connector described in claim 1, wherein a conduit is connected to one end of the fluid passage of the suction connector.

* * * * *